(12) United States Patent
Dresselhaus et al.

(10) Patent No.: US 7,836,910 B2
(45) Date of Patent: Nov. 23, 2010

(54) SOIL MOISTURE SENSOR AND CONTROLLER

(75) Inventors: Daniel D. Dresselhaus, Sierra Madre, CA (US); Kevin G. O'Brien, Pasadena, CA (US)

(73) Assignee: Rain Bird Corporation, Azusa, CA (US)

( * ) Notice: Subject to any disclaimer, the term of this patent is extended or adjusted under 35 U.S.C. 154(b) by 849 days.

(21) Appl. No.: 11/097,061

(22) Filed: Mar. 31, 2005

(65) Prior Publication Data
US 2006/0144438 A1    Jul. 6, 2006

Related U.S. Application Data

(63) Continuation-in-part of application No. 11/027,355, filed on Dec. 29, 2004, now abandoned.

(51) Int. Cl.
 G05B 11/00 (2006.01)
 G01N 25/56 (2006.01)
(52) U.S. Cl. .......................... 137/78.3; 73/73
(58) Field of Classification Search ............... 73/73, 73/74; 137/78.3
 See application file for complete search history.

(56) References Cited

U.S. PATENT DOCUMENTS

| | | |
|---|---|---|
| 3,802,268 A | 4/1974 | Thoma |
| 4,845,421 A | 7/1989 | Howarth et al. |
| 4,850,386 A | 7/1989 | Bireley |
| 4,875,498 A | 10/1989 | Andrews et al. |
| 4,936,333 A | 6/1990 | Bireley |
| 4,941,501 A | 7/1990 | Bireley |
| 5,424,649 A | 6/1995 | Gluck et al. |
| 5,445,176 A | 8/1995 | Goff |
| 5,546,974 A | 8/1996 | Bireley |
| 5,621,669 A | 4/1997 | Bjornsson |

(Continued)

FOREIGN PATENT DOCUMENTS

AT    403 213 B    12/1997

(Continued)

OTHER PUBLICATIONS

PCT; App. No. PCT/US2005/047372; International Preliminary Report on Patentability mailed on Mar. 24, 2009.

(Continued)

Primary Examiner—John Fitzgerald
(74) Attorney, Agent, or Firm—Fitch Even Tabin & Flannery

(57) ABSTRACT

Moisture sensor devices and methods associated with operation of the moisture sensor devices are disclosed herein. One embodiment includes a moisture sensor and controller device adapted to be placed in soil comprising a switch adapted to be coupled to a power control line of an irrigation controller, the power control line for sending an activating power signal to an irrigation valve; a control circuit coupled to the switch; and a sensor circuit coupled to the control circuit and adapted to provide a signal to the control circuit, the signal corresponding to a moisture level of the soil; wherein the control circuit is adapted to control the switch to interrupt the activating power signal based on the signal from the sensor circuit; wherein the switch and the control circuit are both external to the irrigation controller.

40 Claims, 11 Drawing Sheets

U.S. PATENT DOCUMENTS

| | | |
|---|---|---|
| 5,908,045 A | 6/1999 | Wallace et al. |
| 6,016,971 A | 1/2000 | Welch et al. |
| 6,249,130 B1 | 6/2001 | Greer |
| 6,283,139 B1 | 9/2001 | Symonds et al. |
| 6,340,892 B1 * | 1/2002 | Rynhart et al. .............. 324/640 |
| 6,401,742 B1 | 6/2002 | Cramer et al. |
| 6,657,443 B2 | 12/2003 | Anderson |
| 6,756,793 B2 | 6/2004 | Hirono et al. |
| 2003/0015024 A1 | 1/2003 | Campbell et al. |
| 2003/0160107 A1 | 8/2003 | Harris |

FOREIGN PATENT DOCUMENTS

| | | |
|---|---|---|
| DE | 196 16715 A1 | 4/1996 |
| WO | WO 2004/040415 A2 | 5/2004 |
| WO | 2006/071967 A2 | 7/2006 |
| WO | 2006/071967 A3 | 7/2006 |

OTHER PUBLICATIONS

PCT; App. No. PCT/US2005/047372; Written Opinion mailed on Aug. 14, 2008.

US 6,552,552, 04/2003, Hirono et al. (withdrawn)

* cited by examiner

SOIL MOISTURE SENSOR AND CONTROLLER

RELATED APPLICATIONS

This application is a continuation-in-part of U.S. patent application Ser. No. 11/027,355, filed Dec. 29, 2004, entitled CAPACITANCE-BASED MOISTURE SENSOR AND CONTROLLER, to Dresselhaus et al., which application is incorporated herein by reference in its entirety.

BACKGROUND OF THE INVENTION

1. Field of the Invention

The present invention relates to moisture sensors for use in irrigation. More specifically, the present invention relates to capacitance-based moisture sensors.

2. Discussion of the Related Art

Generally, in irrigation systems utilizing a moisture sensor, a moisture sensor is placed in the ground that outputs information about a moisture level of surrounding soil to an irrigation controller in a separate location. The irrigation controller is typically coupled to and controls multiple valves that control water flow to one or more sprinkler devices. The irrigation controller processes the information received from the sensor and modifies a watering cycle for one or more valves based upon the moisture sensor measurements, e.g., when the soil reaches a given moisture content, further irrigation is prevented. In many irrigation systems, the controller uses a single moisture sensor for all of the zones (a zone generally defined as an area watered by a given valve) within the irrigation system. This is a problem when, for example, different zones have different soil types or are exposed to a different amount of sunlight or weather conditions than the soil in which the moisture sensor is located.

Capacitance based moisture sensors generally operate by immersing two electrodes in soil, which forms a dielectric around the electrodes. The capacitance generated between the electrodes varies with the dielectric constant of the soil (which is known to vary with moisture content). However, known capacitance based sensors operate unreliably and are influenced by factors such as variations in temperature and supply voltage.

SUMMARY OF THE INVENTION

Several embodiments of the invention provide a capacitance based moisture sensor and controller that is coupled to irrigation valves for use in irrigation systems.

One embodiment includes a moisture sensor and controller device adapted to be placed in soil comprising a switch adapted to be coupled to a power control line of an irrigation controller, the power control line for sending an activating power signal to an irrigation valve; a control circuit coupled to the switch; and a sensor circuit coupled to the control circuit and adapted to provide a signal to the control circuit, the signal corresponding to a moisture level of the soil; wherein the control circuit is adapted to control the switch to interrupt the activating power signal based on the signal from the sensor circuit; wherein the switch and the control circuit are both external to the irrigation controller.

One embodiment can be characterized as an integrated moisture sensor and controller device adapted to be placed in soil comprising a controller circuit for controlling actuation of a valve; and a sensor circuit coupled to the controller circuit, the sensor circuit adapted to provide the controller circuit a signal corresponding to a moisture level of the soil; wherein the controller circuit and the sensor circuit are integrated into a single device.

Another embodiment includes an integrated moisture sensor and controller comprising a housing adapted to be positioned in soil; a sensor coupled to the housing, the sensor adapted to measure a moisture level in the soil; and a control circuit coupled to the sensor, the control circuit contained within the housing and adapted to store a savings value corresponding to an amount of water savings, wherein the sensor and the controller are integrated into a single device.

Yet another embodiment includes a moisture sensor unit for use in soil comprising a probe adapted to be inserted into the soil, wherein the probe is adapted to be responsive to a moisture level in the soil; and a first protrusion coupled to the probe and adapted to maintain the probe in a desired orientation within the soil.

In one embodiment, the invention can be characterized as a moisture sensor device comprising: a probe forming a capacitor and adapted to be positioned within soil; a controller coupled to the probe, the controller comprising a variable frequency oscillator, the frequency of the variable frequency oscillator varies as a function of a capacitance of the probe, the capacitance varies as a function of a moisture content of the soil; a reference oscillator; and a circuit for comparing the frequency of the variable frequency oscillator to a frequency of the reference oscillator; and a switch coupled to the circuit and adapted to be coupled to a power output line of an irrigation controller and a power actuation line coupled to a valve.

In another embodiment, the invention can be characterized as an irrigation system comprising an irrigation controller adapted to execute water schedules and output power signals to active and deactivate valves; a moisture sensor electrically coupled to the controller comprising a probe forming a capacitor and adapted to be positioned within soil; a controller coupled to the probe, the controller comprising a variable frequency oscillator, the frequency of the variable frequency oscillator varies as a function of a capacitance of a capacitor, the capacitance varies as a function of a moisture content of the soil; a reference oscillator; and a circuit for comparing the frequency of the variable frequency oscillator to a frequency of the reference oscillator; and a switch coupled to the circuit and adapted to be coupled to a power output line of the irrigation controller and a power actuation line; and a valve electrically coupled to the power actuation line.

In a subsequent embodiment, the invention can be characterized as an integrated moisture sensor and controller device adapted to be placed in soil comprising a housing; a controller circuit within the housing for controlling actuation of a valve; and a sensor circuit within the housing and coupled to the controller circuit, the sensor circuit adapted to provide the controller circuit a signal corresponding to a moisture level of the soil.

In yet another embodiment, the invention can be characterized as a method of calibrating a moisture sensor comprising positioning the moisture sensor into a medium; applying power to the moisture sensor; and storing a value in a memory of the moisture sensor, the value corresponding to a current moisture level of the medium.

In another embodiment, the invention can be characterized as a moisture sensor device comprising a probe forming a capacitor and adapted to be positioned within soil; a controller coupled to the probe, the controller comprising a threshold circuit adapted to determine a moisture content of the soil, the capacitance of the probe varying as a function of the moisture content of the soil; and a communication circuit adapted to receive communications from an electronic device over a power output line of an irrigation controller, the communications including a command to adjust a setting of the moisture sensor; and a switch coupled to the circuit and adapted to be coupled to the power output line of an irrigation controller and a power actuation line coupled to a valve.

In an alternative embodiment, the invention includes an electronic device comprising a switch coupled to a power line of moisture sensor and adapted to interrupt power to the moisture sensor; and a controller coupled to the switch and adapted to control the power interruptions of the switch, wherein the power interruptions include communications to the moisture sensor, the communications including a command to adjust a setting of the moisture sensor.

In another alternative embodiment, the invention includes an integrated moisture sensor and controller comprising a housing adapted to be positioned in soil; a sensor contained within the housing, the sensor adapted to measure a moisture level in the soil; and a controller coupled to the sensor and contained within the housing, the controller adapted to store a savings value corresponding to an amount of water savings.

Another embodiment can be characterized as a method of controlling a valve comprising comparing a frequency of a variable frequency oscillator that varies as a function of a capacitance of a probe positioned in soil to a frequency of a reference oscillator, wherein the capacitance of the probe varies as a function of a moisture content of the soil; determining if the moisture content of the soil exceeds a threshold level; and controlling a switch that is coupled to a valve solenoid through a power actuation line.

Still another embodiment can be characterized as a self calibrating moisture sensor device comprising a probe adapted to be positioned in soil; a controller circuit coupled to the probe and adapted to take a moisture sensor reading upon receiving power; and a memory coupled to the controller circuit and adapted to store a value in a memory of the moisture sensor, the value corresponding to a current moisture level of the medium.

Another embodiment includes a method of communicating with an electronic device comprising receiving communications from the electronic device over a power output line of an irrigation controller at a moisture sensor; and adjusting a setting of the moisture sensor in response to the received communications.

Another embodiment can be characterized as a moisture sensor unit for use in soil comprising a housing adapted to be inserted into the soil; a probe formed within the housing, the probe adapted to be responsive to a moisture level in the soil; and a first spike extending from the housing and adapted to maintain the housing in a desired orientation within the soil.

BRIEF DESCRIPTION OF THE DRAWINGS

The above and other aspects, features and advantages of the present invention will be more apparent from the following more particular description thereof, presented in conjunction with the following drawings, wherein.

Figure 1:
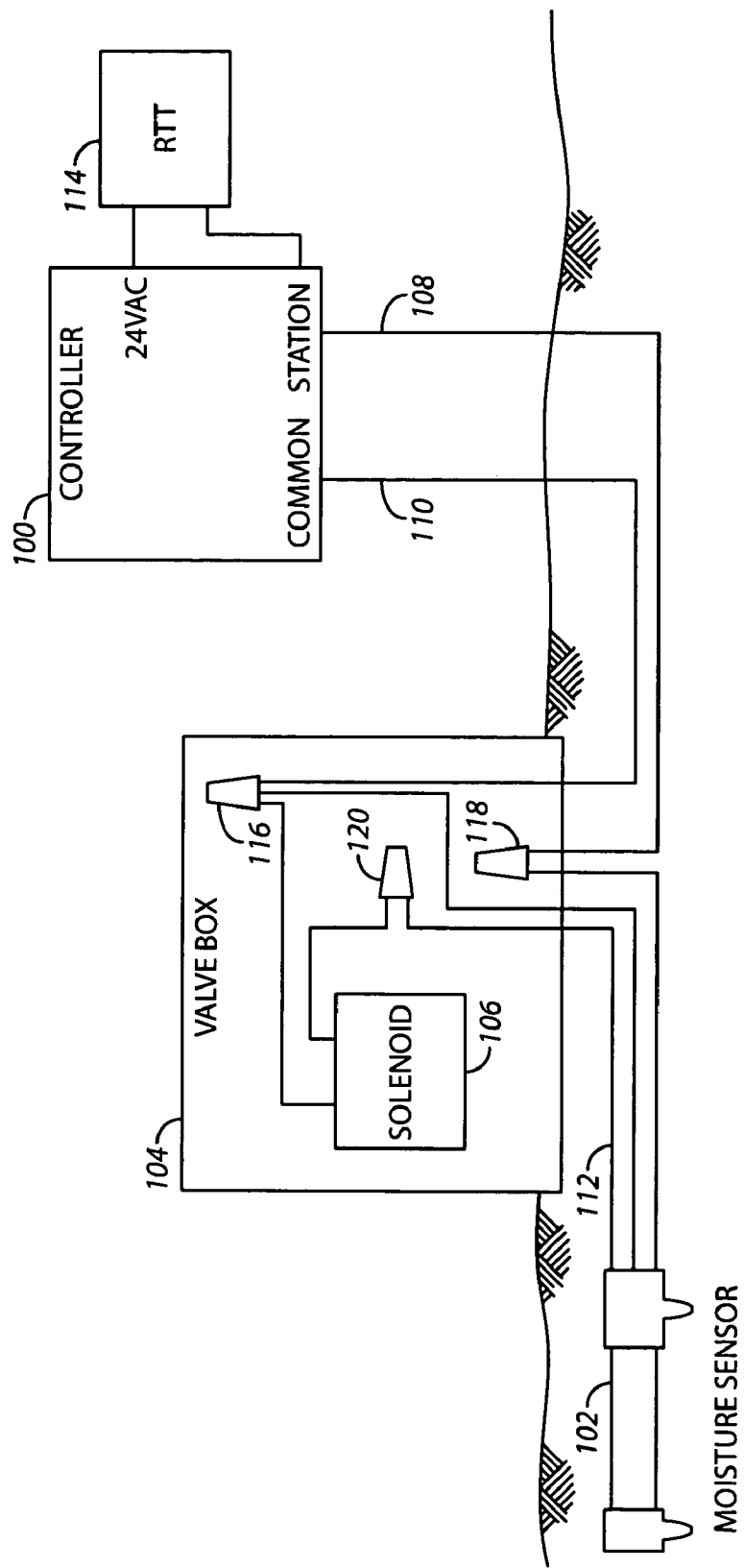
FIG. 1 is a block diagram illustrating an irrigation system in accordance with one embodiment.

Corresponding reference characters indicate corresponding components throughout the several views of the drawings. Skilled artisans will appreciate that elements in the figures are illustrated for simplicity and clarity and have not necessarily been drawn to scale. For example, the dimensions, sizing, and/or relative placement of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will also be understood that the terms and expressions used herein have the ordinary meaning as is usually accorded to such terms and expressions by those skilled in the corresponding respective areas of inquiry and study except where other specific meanings have otherwise been set forth herein.

DETAILED DESCRIPTION

The following description is not to be taken in a limiting sense, but is made merely for the purpose of describing the general principles of the invention. The scope of the invention should be determined with reference to the claims. The present embodiments and examples address the problems described in the background while also addressing other additional problems as will be seen from the following detailed description.

Referring to FIG. 1 a block diagram is shown illustrating an irrigation system in accordance with one embodiment. Shown is an irrigation controller 100, a sensor 102 (also referred to herein as a moisture sensor unit), a valve box 104, a solenoid valve 106 (also referred to as a valve), a power line 108, a common line 110, an actuation line 112, a remote test tool 114, a first connector 116, a second connector 118, and a third connector 120.

The valve box 104 houses the solenoid valve 106. As referred to herein the solenoid valve 106 is a valve that is actuated by a solenoid. The irrigation controller 100 is connected to the moisture sensor unit 102 through the valve box 104. The power line 108 and the common line 110 both run from the controller 100, to the valve box 104 and then to the sensor 102. The sensor 102 is electrically coupled to the solenoid valve 106 with the common line 110 and the actuation line 112. The remote test tool 114 is coupled to the irrigation controller 100 power supply and to the power line 108.

The irrigation controller 100 (generically referred to as an electronic control device) is for example, a zone irrigation controller that controls operation of one or more watering zones. For example, the controller 100 has outputs for controlling up to 8 zones (a solenoid valve 104 and moisture sensor unit 102 for each zone) in one embodiment. FIG. 1 is shown with only one zone for clarification purposes, however, it should be understood that one or more zones can be adapted to include the sensor 102 in accordance with the embodiments described herein. Additionally, the valve box 104 can house one or more solenoid valves 104. In one embodiment, each watering zone includes a sensor 102. Alternatively, one or more watering zones are adapted to include the sensor 102.

The sensor 102 is a moisture sensor buried in the soil that measures a moisture level of the surrounding soil. In one embodiment, each watering zone within an irrigation system has a sensor 102 buried in the soil. In this manner, each watering zone is individually monitored to determine how much water is needed in each zone. In a preferred form, the sensor 102 includes control functionality and acts as a regulator for the watering zone in which the sensor 102 is located. The sensor 102 regulates the amount of water the zone receives by preventing actuation of the solenoid valve 104 based upon a moisture level reading. The sensor 102 is coupled in series between the irrigation controller 100 and the solenoid valve 106. The irrigation controller 100 provides power to the sensor 102. The sensor 102, once supplied power from the irrigation controller 100 supplies power to the solenoid valve 106 so long as the moisture level of the soil is not above a threshold level. The power to the solenoid valve 106 actuates the solenoid valve and allows water to flow to sprinklers (not shown). Thus, the sensor 102, in conjunction with the irrigation controller 100 controls or regulates the operation of the solenoid valve 106 which in turn controls water flowing to sprinklers.

Advantageously, in accordance with the one embodiment, a moisture sensor is provided to monitor a single zone within an irrigation system. An existing irrigation system can easily be modified by placing the moisture sensor unit 102 in series between the irrigation controller 100 and the valve solenoid 106. The moisture sensor unit 102 is connected in series between the controller 100 through the first connector 116, the second connector 118 and the third connector 120. Because the moisture sensor controls the actuation of the solenoid valve 106, existing irrigation systems can be easily modified to include the moisture sensor without the need to replace the controller 100. The controller 100 operates as though providing power to each valve solenoid within the system, however, the moisture sensor unit 102 controls the actuation of the valve solenoid by acting as a switch. Advantageously, the controller 100 can be set such that the watering days and duration for the zone is sufficient water for the maximum requirement for the year. In this manner, the zone will always receive enough water, regardless of the time of year; however, the moisture sensor 102 will prevent the zone from being over-watered at any time. This feature allows a controller to be set for the entire year without any need to reprogram the controller for different times of the year or for different weather conditions. In this manner, the sensor 102 acts as a moisture regulator for the zone in which the sensor is located.

Generally, in prior irrigation systems, the controller 100 is programmed to provide power to a solenoid 106 for a set amount of time (for example, 10 minutes) on specific days of the week (for example, Monday, Wednesday, and Friday). Thus, for the example given, power would be provided to the solenoid 106 three days a week, for 10 minutes on each of the three days. Each watering zone within the irrigation system works in this manner. At different months during the year, different watering times are generally desirable. However, in order to adjust a watering schedule, the controller 100 needs to be reprogrammed. Thus, keeping the soil consistently at a desired moisture level involves reprogramming of the controller 100 throughout the year.

In accordance with the present embodiment, instead of providing power directly to the solenoid valve 106 in order to turn the water on and off, the irrigation controller 100 provides power to the sensor over the power line 108. Providing power to the sensor 102 turns the sensor 102 on and allows the sensor 102 to measure the moisture level in the soil. The sensor 102, in turn, allows power from the controller to continue to the solenoid valve 106 over the actuation line 112 if the moisture level is below a desired level. When the moisture level increases beyond the desired level, the sensor terminates power to the solenoid valve 106, stopping further watering. In this manner, water is only provided to a zone if the soil in the zone is below the desired moisture level. Advantageously, incorporating the sensor 102 located proximate to the solenoid valve 106 provides an accurate moisture level reading for the soil that is currently being watered and thus prevents over-watering of a specific zone within the irrigation system. In this manner, every zone within the irrigation system receives the correct amount of water without having to adjust the watering time for each zone at the controller.

Additionally, during a watering cycle, the sensor 102 monitors the soil moisture and interrupts power to the solenoid 106 if the moisture level of the soil exceeds a threshold level. The threshold level corresponds to the desired moisture level of the soil. In one embodiment, the threshold level of the sensor 102 is set to an offset below a saturated soil moisture level. A calibration process for setting the threshold level is described herein with reference to FIG. 12. Alternatively, the threshold level is pre-programmed into the moisture sensor during production. Additionally, the remote test tool 114 (generically referred to as an electronic control device) can be used to reset or adjust the threshold level. The remote test tool 114 will be described in greater detail herein with reference to FIG. 11.

In one embodiment, the moisture sensor unit 102 (described herein in greater detail with reference to FIGS. 3-10) is an integrated moisture sensor and controller. In another embodiment, the moisture sensor unit 102 acts as a switch between the controller 100 and solenoid valve 106. The moisture sensor unit is also, in one embodiment, an improved capacitance based moisture sensor that is preferably located proximate a watering zone, such that accurate watering of each zone within an irrigation system is accomplished. Additionally, in one embodiment, the moisture sensor unit described herein helps to conserve water in an irrigation system by preventing each zone within the irrigation system from being over-watered. These features will be further described herein below.

Figure 2:
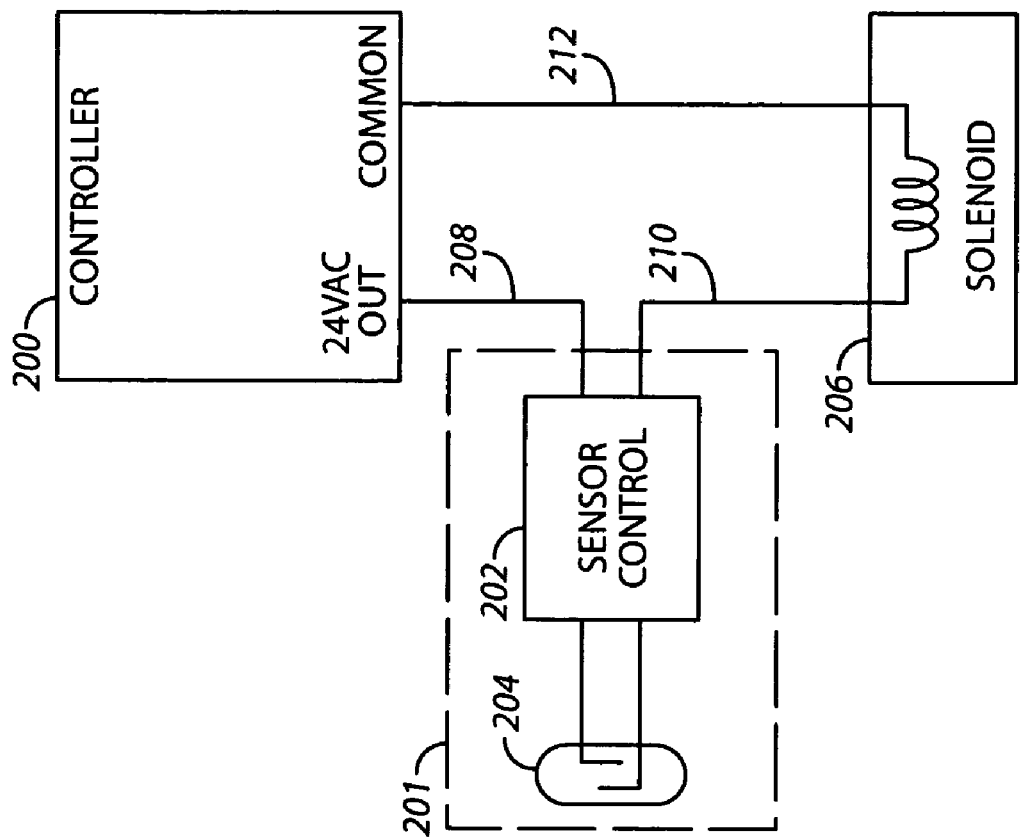
FIG. 2 is a simplified block diagram illustrating the irrigation system of FIG. 1 in accordance with one embodiment.

Referring to FIG. 2, a block diagram is shown illustrating the irrigation system of FIG. 1 in accordance with one embodiment. Shown is an irrigation controller 200 (also referred to as a controller), a moisture sensor device 201, a sensor control 202, a moisture probe 204, a solenoid 206, a power line 208, an actuation line 210, and a common line 212.

The controller 200 is connected in series with the sensor control 202 and the solenoid 206. The sensor control 202 includes the moisture probe 204 and is integrated into a single package, such as is shown in FIGS. 4A-7, in accordance with one embodiment.

The moisture sensor device 201 includes the sensor control 202 and the moisture probe 204. In one embodiment, the moisture sensor device 201 is a single integrated unit including the sensor control 202 and the moisture probe 204. Optionally, the sensor control 202 and moisture probe 204 are implemented on a single circuit board. In an alternative embodiment, the sensor control 202 and the probe 204 are separate devices that are electrically coupled together. The sensor control 202 includes, for example, a logic power supply, a switch, a microcontroller, and a power monitor.

In operation, power is supplied from the controller 200 to the sensor control 202 through the power line 208. The sensor control 202 measures a moisture level of the soil and provides power to the solenoid 206 so long as the measured moisture level in the soil is not above a threshold level. The threshold level is stored, for example, in a non-volatile memory of the sensor control 202. The sensor control 202, when supplied power from the controller 200, controls the operation of the solenoid 206 which in turn actuates a valve (not shown). The valve controls the water flow to sprinklers (not shown). Essentially, the sensor control 202 acts as a switch to allow power from the controller 200 to pass to the solenoid 206 or to block this power from reaching the solenoid 206 In contrast, in prior irrigation systems the solenoid 206 is generally turned on and off directly by the controller 200. It should be understood that the solenoid is one example of an electrical activation device for a valve and that different types of electrical activation devices can be used as the activation device for the valve. Additionally, the term "solenoid actuated valve" shall also encompass valves used in irrigation systems in which a pilot valve is not directly opened and closed by a solenoid. These include hydraulically or pneumatically actuated valves which have a solenoid or its electrical equivalent somewhere in the fluid system, and not necessarily next to the gating valve, for controlling the fluid pressure to open and close the valves.

The solenoid 206 is activated when the sensor control 202 provides power on the actuation line 210. Providing power on the actuation line 210 causes the solenoid 206 to open the valve and allows water to flow to the sprinklers. When the sensor control 202 measures a moisture level that is above the threshold level, the sensor 200 interrupts power to the solenoid 206 even when power is supplied to the sensor control 202 from the controller 200. For example, a controller 200 will generally open each valve in a watering system at a predetermined time for a predetermined amount of time according to a preprogrammed watering schedule. The controller can, in one embodiment, receive input from, for example, temperature sensors or other devices that alter the preprogrammed watering schedule. In accordance with the present embodiment, the controller 200 will turn on the sensor control 202 at the same cycle that it would normally open the solenoid 206. The sensor control 202 then measures the moisture level in the ground. If the moisture level in the ground is below the stored threshold level, the sensor control 202 will provide power to the solenoid 206 which causes the valve to open. When the sensor control 202 measures a moisture level in the soil that is at or above the threshold level, the sensor control 202 will stop providing power to the solenoid 206 and the watering will stop. In one form, the sensor control 202 includes a relay or switch that is opened, which prevents the power signal from the controller 200 from reaching the solenoid. The sensor control 202 thus can stop the watering before the controller 200 would normally have turned the valve off. This prevents the soil from becoming oversaturated because of too much watering. Additionally, during a heavy rain, the sensor can prevent the valve from ever being opened. Thus, the controller 200 does not need to be adjusted to stop watering during a rainy day. Advantageously, the moisture sensor control 202 keeps the soil at a desired moisture level and also helps to conserve water by preventing watering zones from being over-watered.

In one embodiment, the sensor will turn on the water for a minimum time (for example 30 seconds) in each zone in order to indicate that the controller 200, sprinklers and sensor control 202 are working properly.

Figure 3:
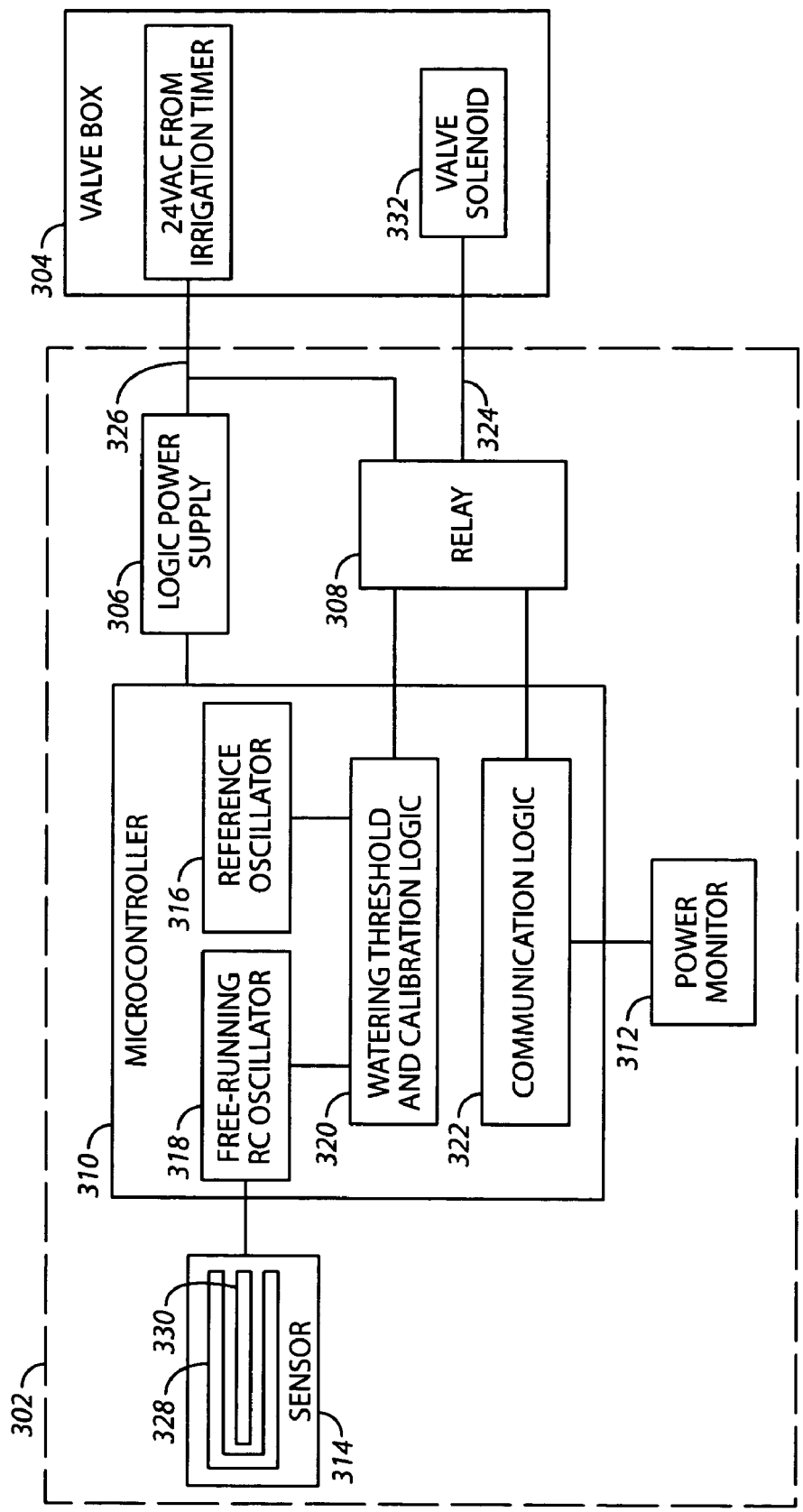
FIG. 3 is a functional block diagram illustrating the irrigation system and moisture sensor unit of FIG. 1 in accordance with one embodiment.

Referring to FIG. 3, a detailed block diagram is shown illustrating the irrigation system and moisture sensor of FIG. 1 in accordance with one embodiment. Shown is a moisture sensor unit 302, a valve box 304, a logic power supply 306, a switch 308, a microcontroller 310, a power monitor 312, a probe 314, a reference oscillator 316, a free-running oscillator 318 (also referred to as a variable frequency oscillator), a watering threshold and calibration module 320, a communication module 322, an actuation line 324, a power line 326, a first trace 328, a second trace 330 and a valve 332.

The moisture sensor unit 302 includes the logic power supply 306, the switch 308, the microcontroller 310, the power monitor 312, and the probe 314. The microcontroller 310 includes the reference oscillator 316, the free-running oscillator 318, the watering threshold and calibration module 320, the communication module 322. The microcontroller additionally has memory (not shown) for storing commands and also for storing data, such as the moisture content threshold level. The probe 314 includes the first trace 328 and the second trace 330.

The valve box 304 is connected to the microcontroller 302 through the power line 326 and the actuation line 324. The valve box 304 houses the valve 332. In one embodiment, the valve 332 is a solenoid controlled valve. A common line is not shown in the valve box, however, it should be understood that the common line is optionally coupled between the sensor unit 302 and the valve 332. It should also be understood that the actuation line is electrically coupled to a solenoid which actuates the valve 332 upon receiving a power signal.

In one embodiment, the sensor unit 302 in encased in a housing, for example, a plastic housing or epoxy housing. The housing can include one or more components, however, the housing is preferably waterproof such that no metal components of the moisture sensor unit 302 is exposed to moisture. This allows the moisture sensor to last for years buried in soil without failing due to rusting of metal components or other problems that moisture can cause in electrical devices. Optionally, all of the components of the moisture sensor unit 302 (i.e., the logic power supply 306, the switch 308, the microcontroller 310, the power monitor 312, and the probe 314) are formed onto a single circuit board. The circuit board is the encapsulated in the watertight housing. Alternatively, a thin coating made from an insulating material is applied to the circuit board. Still alternatively, a multi-layered circuit board is utilized having the first trace 328 and the second trace 330 of the probe 314 formed on an inner layer of the multi-layered circuit board. These various embodiments, described in greater detail herein below, provide for a compact moisture sensor and controller that can be easily added to most any irrigation system without the need to modify other components of the irrigation system.

In operation, power (for example, 24 volt AC power) is provided from a controller (shown in FIGS. 1 and 2) to the moisture sensor 302 over the power line 326. The logic power supply 306 converts the 24 volt AC power into a constant DC voltage that is used to power the microcontroller 310. The microcontroller 310 includes the reference oscillator 316 and the free running oscillator 318. The free-running oscillator 318 and the fixed frequency reference oscillator 316 can produce many types of waveforms. In one embodiment, the free-running oscillator 318 and the fixed frequency reference oscillator 316 produce triangular wave forms. However, the free running oscillator 318 and the fixed frequency reference oscillator 316 optionally produce, for example, square wave or sinusoidal wave forms. Additionally, the free-running oscillator 318 and the fixed frequency reference oscillator 316 do not need to produce the same type of waveform. For example, the free-running oscillator 318 can produce a triangular wave and the fixed frequency reference oscillator 316 can produce a square wave in accordance with one embodiment. The free running oscillator 318 is connected to the probe 314 which includes the first trace 328 and the second trace 330.

The first trace 328 and the second 330 act as two plates of a capacitor. Soil and water act as the dielectric between the two plates of the capacitor. Dry soil generally has a dielectric constant of about 4 to 5 and water generally has a dielectric constant of about 80. Thus, changes in the volumetric water content of the soil create large changes in the dielectric properties and therefore in the capacitance generated between the first trace 328 and the second trace 330 of the probe 314. The free running oscillator 318 changes frequency (i.e., has a variable frequency) depending upon the capacitance of the probe 314. The frequency of the free-running oscillator 318 is compared to the fixed frequency reference oscillator 316 in order to give an indication of the moisture level of the soil. Because both of the oscillators (i.e., the reference oscillator 316 and the free-running oscillator 318) have the same power supply and are located within the same microcontroller in one embodiment, variations in the temperature or supply voltage will have little effect on the moisture level reading, as both of the oscillators will be affected by the same external influences. That is, the frequency of the reference oscillator 316, while generally fixed, may vary with variations in temperature of the moisture sensor unit 302 or power supply voltage, however, the free-running oscillator 318 will also vary generally in the same manner. By comparing the frequency of the free-running oscillator 316 to the frequency of the reference oscillator 318, a determination is made by the watering threshold and calibration module 320 as to whether the moisture content of the soil has exceeded the stored threshold level. If the moisture level is below the threshold level, the microcontroller activates the switch 308. Subsequently, the switch 308 provides power received on the power line 326 to the valve 332 over the actuation line 324. This power opens the valve 332 and allows for watering of the zone. In other words, the microcontroller closes a switch connecting the power line 326 to the actuation line 324.

After the valve is open and watering has begun, the moisture level in the soil will change, which causes the capacitance of the probe 314 to change, thus causing a change in the frequency of the free-running oscillator 318. When the moisture content of the soil reaches the threshold level, the watering threshold and calibration module 320 deactivates the relay 324, causing the valve to close and terminate further watering.

The communication module 322 can communicate with a remote or external device that is external to the sensor unit 302, such as a remote test tool (shown in FIGS. 1 and 11) or the controller (such as controller 100 or 200). The communication module sends information to the remote test tool by producing AC pulses on the actuation line 324 to the valve solenoid 322. This causes a change in the current from the controller to the moisture sensor unit that can be detected by the remote test tool. This allows the remote test tool to gather information from the moisture sensor unit 302 such as, for example, the current threshold level, the current moisture level, and a percentage of water savings. The remote test tool is also used to reset all values in the moisture sensor unit 302 to a default and adjust the threshold level. In one embodiment, data is sent and received from the sensor as a series of 50 millisecond AC pulses at 500 millisecond intervals. The communication module includes an encoder and a decoder in accordance with one embodiment. The encoder and decoder provide the ability to encode data into the series of pulses and decode received pulses into data, respectively. Other types of communication protocols can be used with the present embodiments. In one embodiment, the AC pulses are power interruptions in the power signals sent to the moisture sensor unit 302. The power monitor 312 detects the power interruptions from, for example, an irrigation controller or the remote test tool and signals to the communication module 322 that the power interruption has been detected. The communication module 322 interprets the power interruptions and takes appropriate action. The different types of communications are described in greater detail herein with reference to FIG. 12.

In one embodiment, the controller includes circuitry that calculates and stores a savings value that corresponds to an amount of water savings. The savings value, for example, corresponds to an amount of water saved, for example, a number of gallons of water. Alternatively, the saving value corresponds to a percentage of water savings. The percentage water savings is calculated, in one embodiment, by the moisture sensor unit by taking the total time that power to the valve is interrupted by the moisture sensor unit divided by the total time that the moisture sensor unit is provided power from the controller.

In the moisture sensor unit 302, the power line goes directly into the controller. When the power monitor of the moisture sensor unit 302 detects a power interruption and tells the controller that there has been an interruption. The controller then determines what to do based upon the detected power interruptions. For example, the controller can adjust a threshold level, enable the sensor and disable the sensor.

Figure 4:
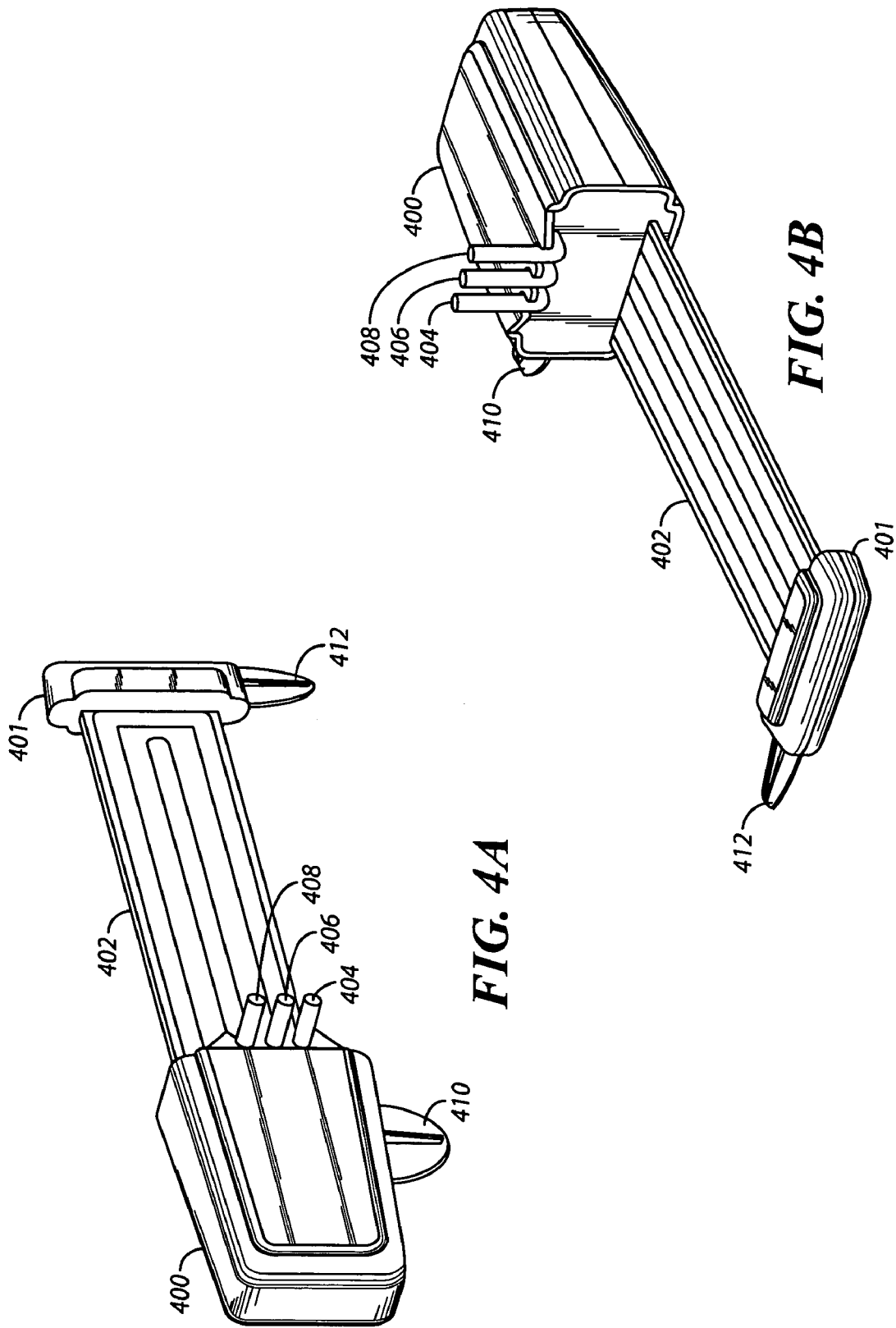
FIG. 4A is a perspective view illustrating a moisture sensor unit in accordance with one embodiment.
FIG. 4B is a second perspective view illustrating the moisture sensor unit shown in FIG. 4A.
Figure 5:
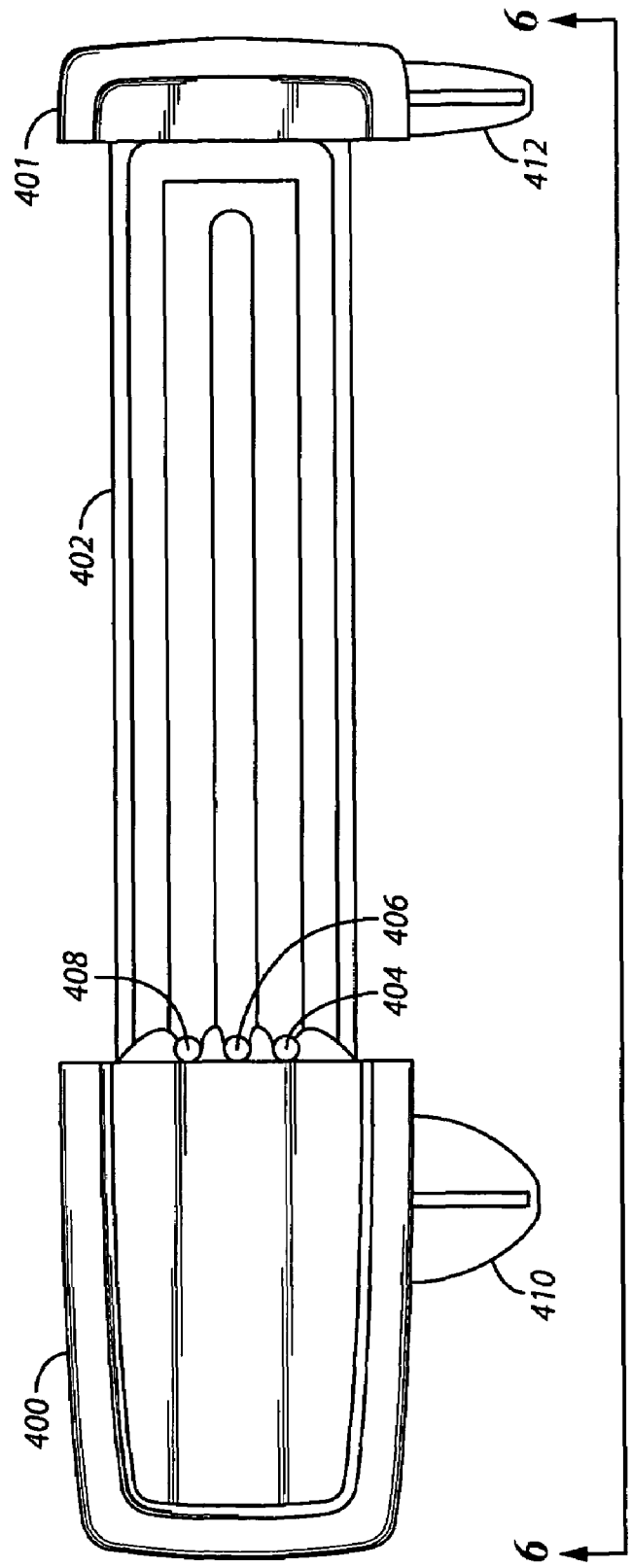
FIG. 5 is a front view of the moisture sensor unit illustrated in FIG. 4 in accordance with one embodiment.
Figure 6:
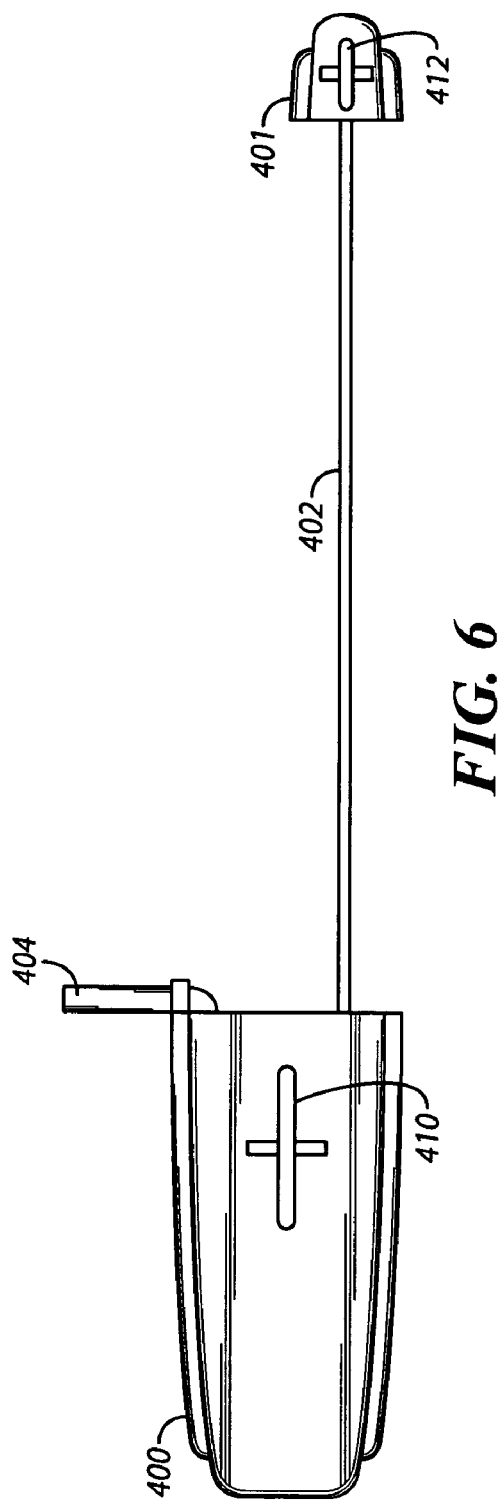
FIG. 6 is bottom view of the moisture sensor unit illustrated in FIG. 4 in accordance with one embodiment.

Referring to FIG. 4A a perspective view is shown illustrating a moisture sensor unit in accordance with one embodiment. FIG. 4B is a second perspective view illustrating the moisture sensor unit of FIG. 4A from an alternate view point. FIG. 5 is a front view of the moisture sensor unit illustrated in FIG. 4. FIG. 6 is bottom view of the moisture sensor unit illustrated in FIG. 4. Shown is a housing that includes a cap 400, an end cap 401 and a probe portion 402. Also shown is a power line connector 404, a common line connector 406, an actuation line connector 408, a first spike 410 and a second spike 412.

The housing forms a watertight enclosure around the functional circuitry of the moisture sensor unit and the probe. In the embodiment shown, the functional circuitry is enclosed in the cap 400 and the probe is enclosed by the probe portion 402 of the housing. The probe portion 402 of the housing is a thin watertight coating formed around a circuit board (e.g., either a single layer or multi-layer circuit board). Optionally, the end cap 401 is not included in the moisture sensor unit and the housing includes only the cap 400 and the probe portion 402. The watertight enclosure ensures the moisture sensor unit is protected from corrosion. In one embodiment, watertight enclosure ensures the moisture sensor unit functions properly while buried in soil for 10 years. The watertight enclosure is made from an epoxy, however, other watertight materials such as plastic are used in alternative embodiments. The housing is used to enclose, for example, the moisture sensor unit shown in FIG. 3. In one embodiment, the housing prevents any metal components from being exposed which in turn prevents any corrosion from taking place.

The probe, in one embodiment is a circuit board with two electrodes formed thereon that form two plates of a capacitor. Additionally, in the illustrated embodiment, the functional circuitry of the moisture sensor unit (for example, the microprocessor 310, logic power supply 306, switch 308 and power monitor 312 shown in FIG. 3) are encased in the cap 400 of the housing. The functional circuitry is also placed on the circuit board with the two electrodes in accordance with one embodiment. This provides a compact and integrated moisture sensor and controller on a single circuit board that is encased in a watertight enclosure.

In another embodiment, the housing includes the cap 400 and end cap 401. The probe portion 402 is a multi-layered circuit board with the two electrodes formed on an inner layer of the circuit board. The electrodes are thus kept from being exposed to the soil by the outer layers of the circuit board. In this embodiment, as is best shown in FIG. 4B, the cap 400 is filled with, for example, a potting material such as an epoxy that encases and protects the functional circuitry of the moisture sensor unit. The end cap 401 is a molded plastic component that is adhered, bonded, or otherwise rigidly attached to the end of the multi-layered circuit board opposite the cap 400. Alternatively, the end cap 401 is not included in the moisture sensor unit and the housing comprises only the cap 400 that enclosed the functional circuitry on the circuit board. Optionally, a thin coating is applied over the multi-layer circuit board in order to further protect the circuit board and the two electrodes from corrosion. Additionally, the thin coating can be utilized with a single layer circuit board having electrodes formed on an exposed surface of the circuit board or when the electrodes are formed on an outer layer of a multi-layer circuit board. The thin coating is an insulating material made from any number of materials, for example, epoxy, fiberglass or urethane. The thin coating is between 0.015 inches and 0.020 inches thick in one embodiment, however, thicker or thinner coatings are used for the thin coating. Still alternatively, a plastic (e.g., polyvinyl chloride (PVC)) sleeve is place over the circuit board in order to insulate the probe portion 402 from the soil.

In one embodiment, the cap 400 is a molded piece of plastic including slots on the inside of the cap 400 that the circuit board slides into during assembly. The end of the circuit board containing the functional circuitry is placed inside the cap 400. Next, the cap 400 is filled with a potting material, for example, an epoxy that insulates the functional circuitry on the circuit board. Optionally, the thin coating is applied to the circuit board (either single layer or multi-layer) before or after being inserted into the cap 400. Finally, the optional end cap 402 is rigidly fixed to the circuit board at the opposite end of the circuit board from the cap 400.

The first spike 410 is a protrusion that is attached to and extends from the cap 400 and the second spike 412 is a protrusion that is attached to and extends from the end cap 401. In one embodiment only one of the first spike 410 and the second spike 412 are attached to the housing. The first spike 410 and the second spike 412 aid is proper placement of the moisture sensor unit in the ground. It is preferred that the moisture sensor unit is situated in the ground such that the circuit board that the probe 402 is formed upon is vertically situated in the ground. This helps to properly drain the ground around the moisture sensor unit. For example, if the circuit board was placed horizontally in the ground moisture would collect on top of the circuit board and the ground directly below the circuit board would dry out. Thus, the first spike 410 and the second spike 412 are placed into the ground to help secure the moisture sensor unit in the correct orientation. The first spike 410 and the second spike 412 also aid in keeping the moisture sensor unit properly placed in the ground during installation of the moisture sensor unit. For example, after a hole has been dug in the ground the moisture sensor unit is placed in the bottom of the hole. The first spike 410 and the second spike 412 penetrate into the ground at the bottom of the hole. As the hole containing the moisture sensor unit is filled back in with soil, the first spike 410 and the second spike 412 keep the moisture sensor unit from moving, thus keeping the moisture sensor unit properly orientated. In one embodiment, the first spike 410 and the second spike 412 are used with a probe that does not have the functional circuitry located within the moisture sensor unit.

In the embodiment shown, the first spike 410 and the second spike 412 are generally in the shape of a fin and have side supporting structures. Other shapes for the first spike 410 and the second spike 412 are used in alternative embodiments. For example, the first spike 410 and the second spike 412 are formed in the shape of a triangle, a rod, a spear, or shaft and still function to support the moisture sensor unit while placed in the ground and to indicate a correct orientation for installation.

Figure 7:
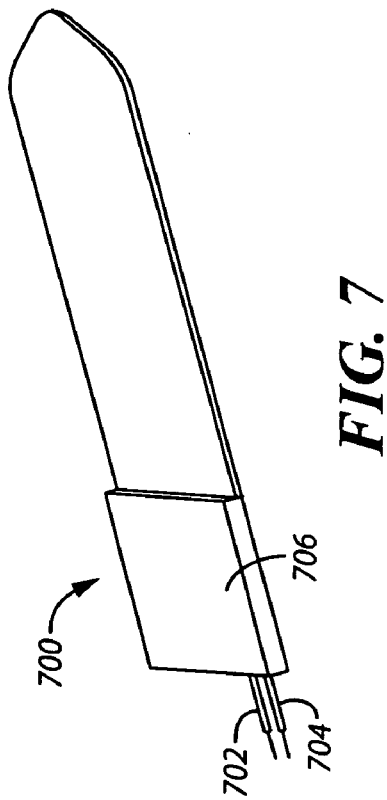
FIG. 7 is a perspective view illustrating a moisture sensor unit in accordance with another embodiment.

Referring to FIG. 7, a perspective view is shown illustrating a moisture sensor unit 700 in accordance with another embodiment. The moisture sensor unit 700 of FIG. 7 includes a power input line 702, a power output line 704 and a water tight housing 706. The moisture sensor 700 can be utilized, for example, in the system described above with reference to FIG. 2. Similar to FIGS. 4-6 the moisture sensor is enclosed in the water tight housing 706 to prevent corrosion.

Figure 8:
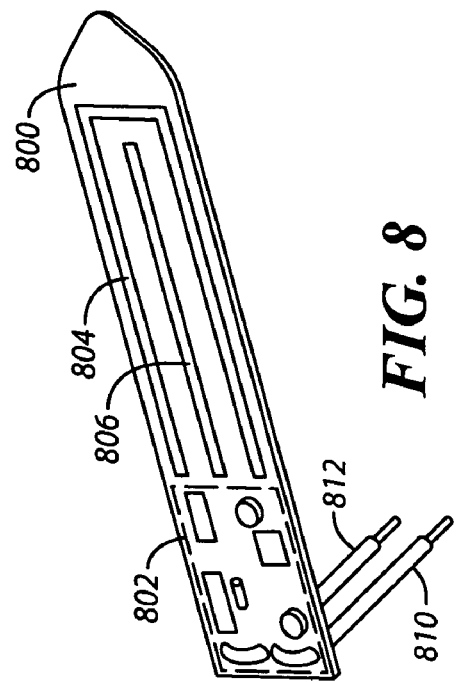
FIG. 8 is a perspective view illustrating a circuit board of the moisture sensor unit shown in FIG. 7 in accordance with one embodiment.

Referring to FIG. 8, a perspective view is shown illustrating a circuit board of the moisture sensor shown in FIG. 7 in accordance with one embodiment. Shown is a circuit board 800, functional circuitry 802, a first trace 804, a second trace 806, a power input line 810 and a power output line 812. The water tight housing 706 shown in FIG. 7 is a molded enclosure that encloses the circuit board 800, the functional circuitry 802, the first trace 804 and the second trace 806 in accordance with one embodiment. The first trace 804 and the second trace 806 are etched onto the circuit board 800 and act as two electrodes of a capacitor. As described above, the capacitance of the capacitor changes with the moisture level in soil. The trace pattern shown is a very simple and inexpensive way to build a capacitor on the circuit board 800. Advantageously, this provides for a moisture sensor and combined controller on a single circuit board. The functional circuitry 802 may include different components, e.g., in one embodiment, the functional circuitry 802 includes the logic power supply 306, the switch 308, the microcontroller 310, the power monitor 312, the probe 314. The circuit board is enclosed in the water tight housing 706 shown in FIG. 7 in accordance with one embodiment.

Figure 9:
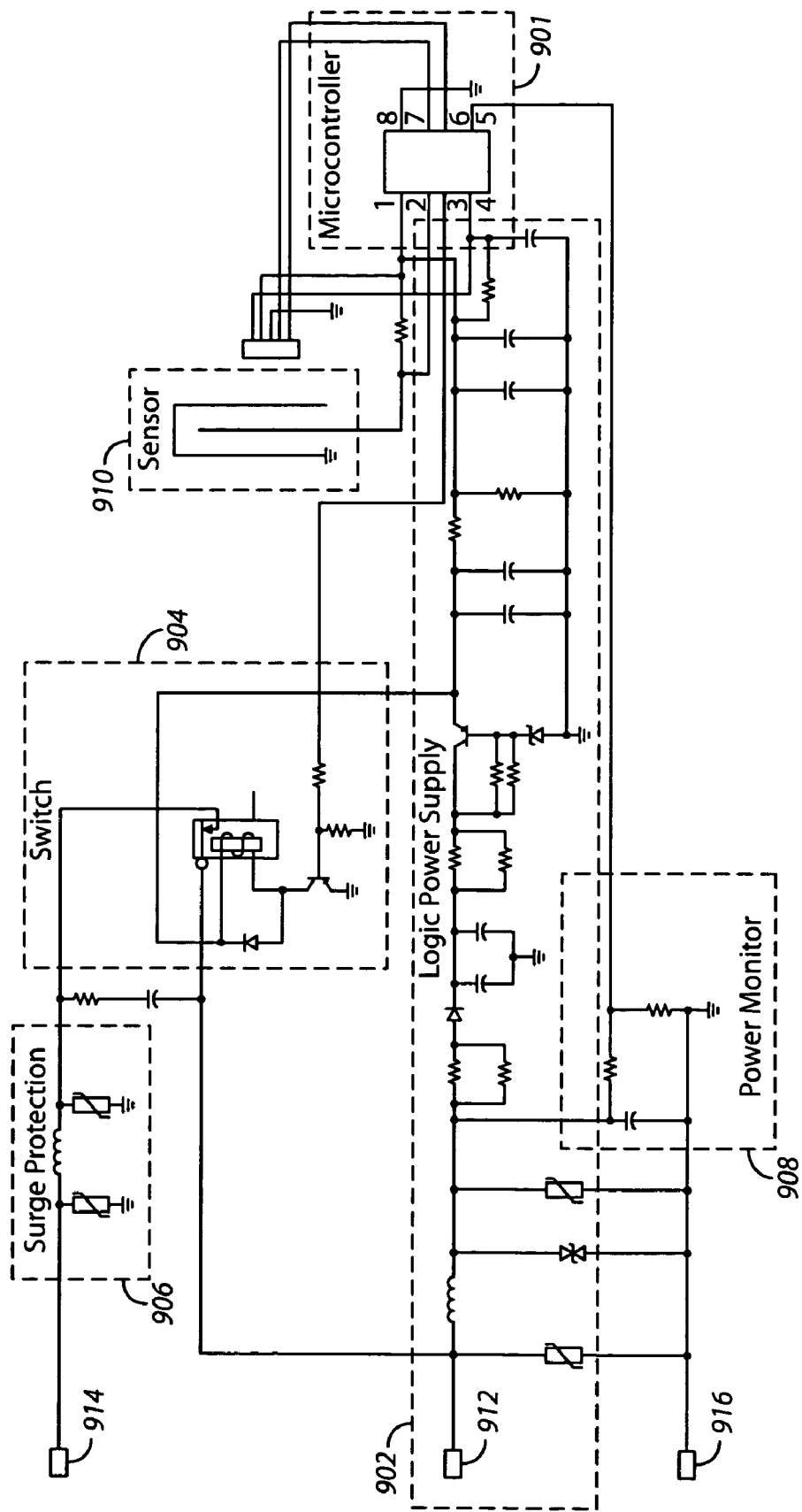
FIG. 9 is a circuit diagram illustrating a moisture sensor unit in accordance with one embodiment.

Referring to FIG. 9, a circuit diagram is shown illustrating a moisture sensor unit 900 in accordance with one embodiment. Shown is a controller circuit 901, a power supply circuit 902, a switch circuit 904, a surge protection circuit 906, a power monitor circuit 908, a probe 910, a power line 912, an actuation line 914 and a common line 916. In one embodiment, the control circuit 901 functions in the same manner as the controller 310 described above with reference to FIG. 3.

The surge protection circuit 906 protects the sensor from surges on a power line, for example, from lightning induced surges. A preferred surge protection circuit is described in U.S. patent application Ser. No. 10/965,945, filed Oct. 14, 2004, entitled POWER SURGE PROTECTION IN AN IRRIGATION CONTROLLER, which is incorporated herein by reference in its entirety. The moisture sensor functions in the same manner as the moisture sensor described with reference to FIG. 3.

Figure 10:
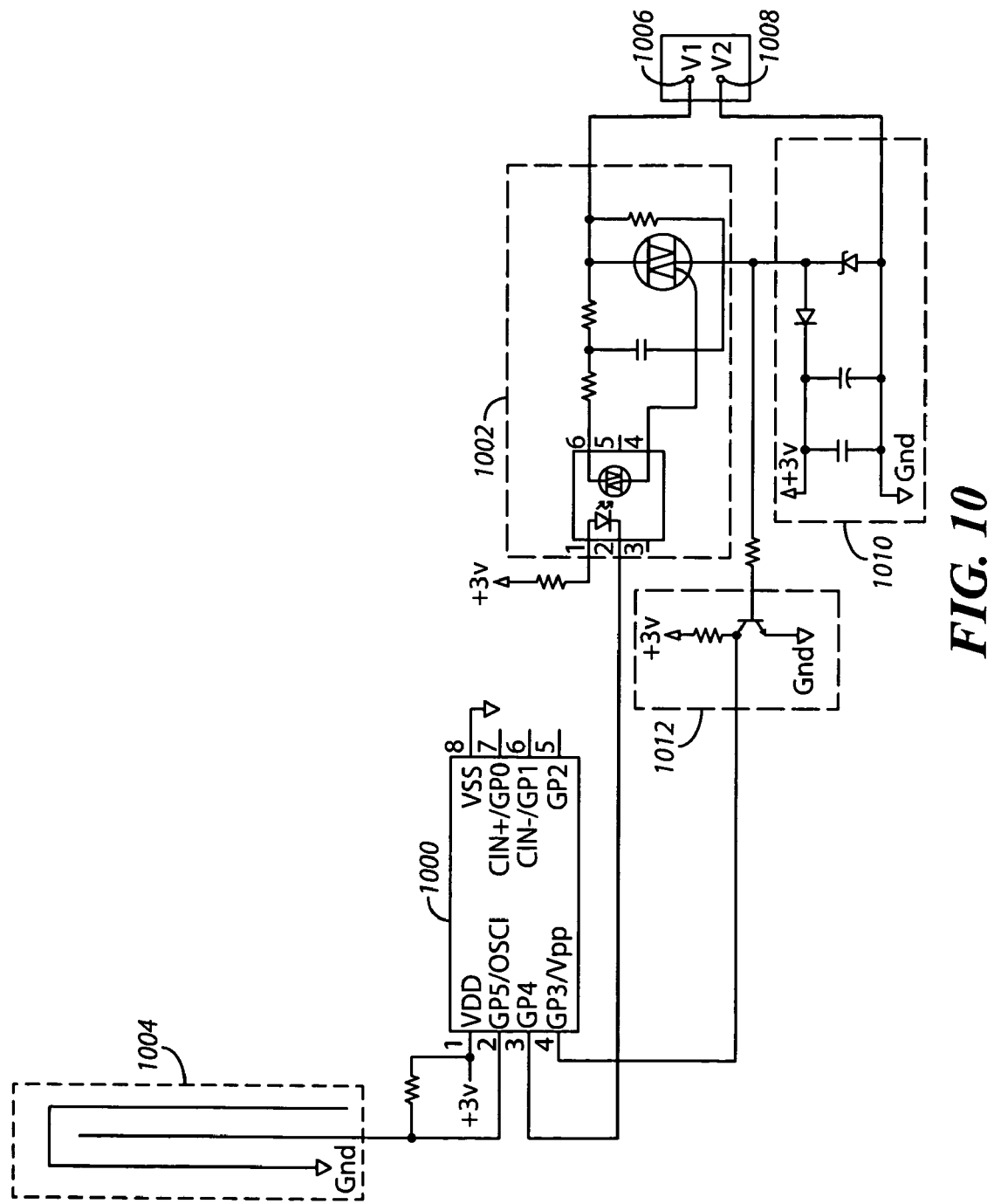
FIG. 10 is a circuit diagram illustrating a moisture sensor unit in accordance with yet another embodiment.

Referring to FIG. 10, a circuit diagram is shown illustrating a moisture sensor in accordance with yet another embodiment. Shown is a controller 1000, a switch 1002, a probe 1004, an input power line connector 1006, an output power line connector 1008, a logic power supply 1010, and the power monitor 1012. The moisture sensor functions the same as the moisture sensor discussed with reference to FIGS. 2 and 8. The controller 1000 includes free running oscillation circuitry that operates between 2 MHz and 10 MHz depending on the moisture level of the surrounding soil. In one embodiment, the controller 1000 also receives a 60 Hz AC signal from the input power line 1006. The 60 Hz AC signal provides a fixed time base signal and is used as a fixed frequency oscillator. The controller 1000 includes circuitry to compare the frequency of the free running oscillator to the frequency of the 60 Hz AC signal, and thus can determine the moisture level of the surrounding soil. When the moisture level of the surrounding soil reaches the threshold level, the microcontroller actives the switch 1002, for example a triac-based AC switch, to stop or start current flow to the valve solenoid. For example, when the switch 1002 is closed power from the input power line connector 1006 flows through the switch 1002 to the output power line connector 1008 and to the valve. When the switch is opened (for example, when the moisture content of the soil has exceeded the threshold level) power is prevented from flowing to the output power line connector 1008 and thus, the valve closes.

Figure 11:
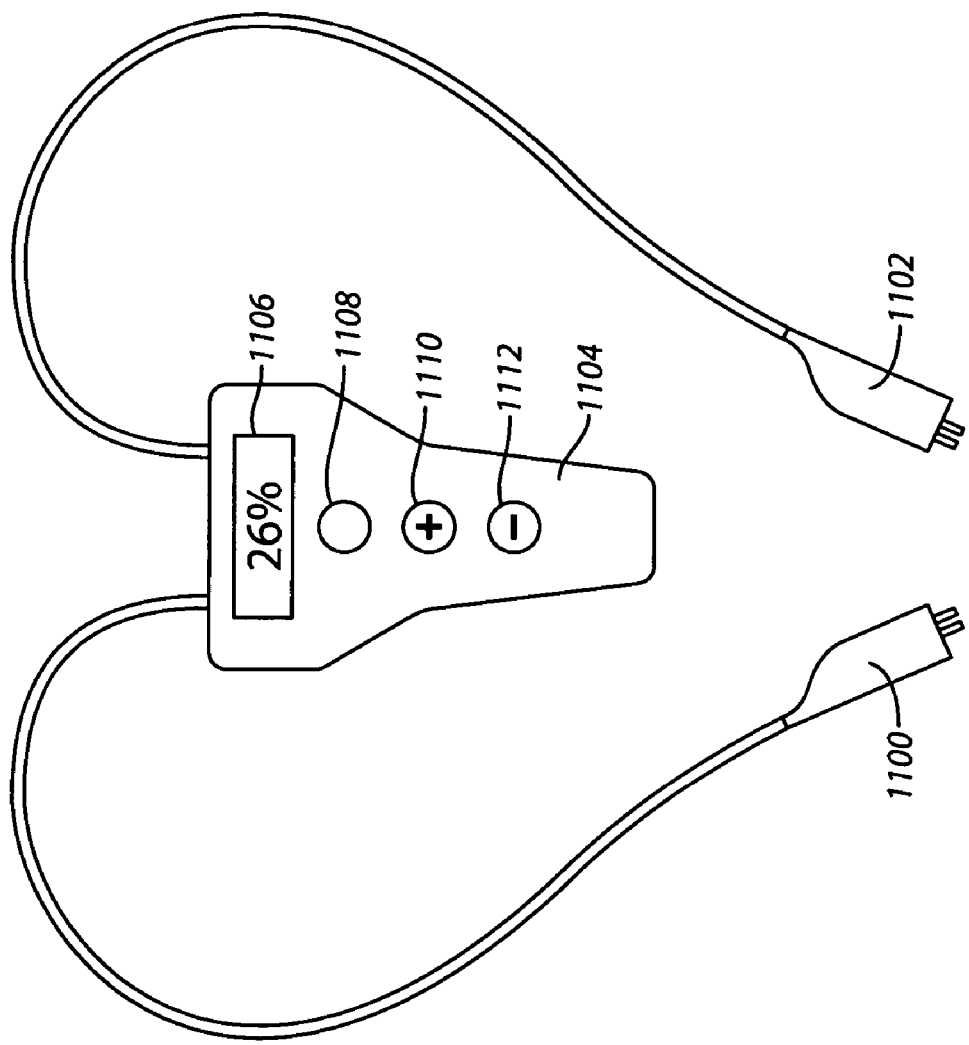
FIG. 11 is a diagram illustrating a remote test tool such as shown in the system of FIG. 1 in accordance with one embodiment.

Referring to FIG. 11, a diagram is shown illustrating a remote test tool (RTT) 1100, such as shown in the system of FIG. 1, in accordance with one embodiment. Shown is an input power line 1101, an output line 1102, an input interface 1104 and a display 1106. The RTT 1100 is used to communicate with a moisture sensor unit such as described herein, for example, with reference to FIG. 3. One or more of the following features can be implemented on the RTT 1100 in accordance with various embodiments.

The RTT 1100 is used to adjust the threshold level of the moisture sensor by sending commands over the power line to the moisture sensor unit. The RTT 1100 is also used to conduct diagnostics on the sensor, initiate a calibration cycle, disable the sensor and modify a threshold level of the sensor. The RTT 1100 also receives data from the moisture sensor unit indicating, for example, a current moisture level or a threshold level. In one embodiment, information is sent to and from the RTT 1100 using series of AC pulses.

In one embodiment, the RTT 1100 is a handheld device that connects to a 24VAC power of the controller and a zone station line using test clips. The RTT 1100 is used to perform diagnostics such as: activating or deactivating a moisture sensor unit, increasing or decreasing a threshold level, displaying water saving data, and resetting the moisture sensor unit to default settings.

In one embodiment, the interface 1104 includes three buttons: a bypass button 1108, a plus water button 1110, and a minus water button 1112. The display 1006 includes a three digit LCD display. When the RTT 1100 establishes communication with the moisture sensor unit and requests a water saving measurement, the moisture sensor unit sends back, for example, a percentage water savings over any number of watering cycles which will be shown on the display 1006. For example, the moisture sensor can send back the percentage water savings over the last 30 watering cycles. The percentage water savings is calculated by the moisture sensor unit by taking the total time that power is interrupted to the valve divided by the total time the sensor is provided power from the controller. In another embodiment, value corresponding to an amount of water savings is stored at the moisture sensor and sent back to the RTT 1100. The plus water button and the minus water button are used to adjust the moisture level measured in the soil before the moisture sensor will shut off the water. This provides for easy adjustment of the moisture sensor after installation.

Figure 12:
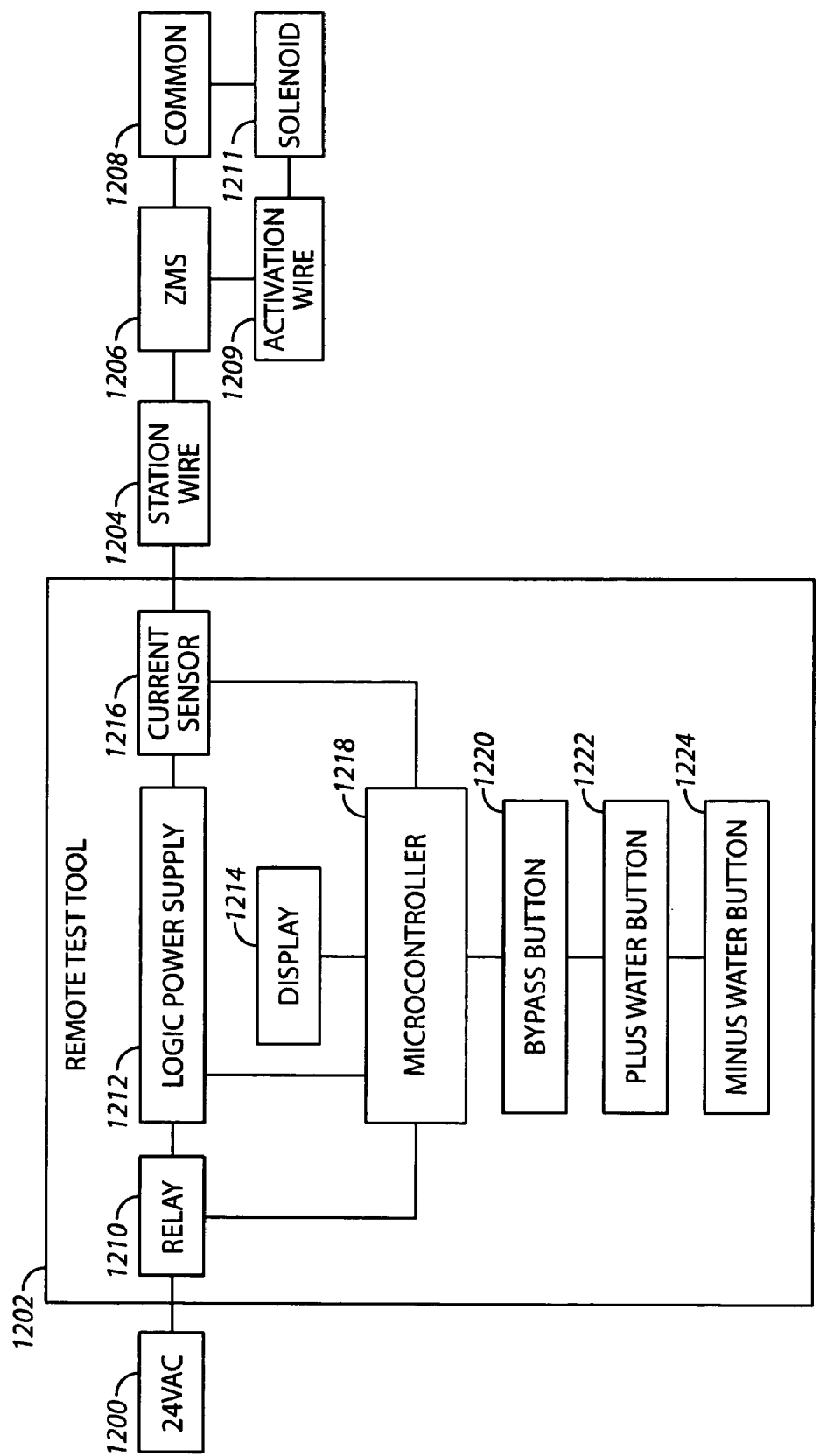
FIG. 12 is a functional block diagram illustrating the remote test tool of FIG. 11 in accordance with one embodiment.

Referring to FIG. 12, a block diagram is shown illustrating the remote test tool of FIG. 11 in accordance with one embodiment. Shown is a power source 1200, a remote test tool 1202, a power line 1204, a moisture sensor unit 1206, a common line 1208, an actuation line 1209, a solenoid 1211, a relay 1210, a logic power supply 1212, a display 1214, a current sensor 1216, a controller 1218, a bypass button 1220, a plus button 1222 and a minus button 1224.

The remote test too 1202 includes the relay 1210, the logic power supply 1212, the display 1214, the current sensor 1216, the controller 1218 the bypass button 1220, the plus button 1222 and the minus button 1224. The relay 1210 is coupled to the logic power supply 1212 and the controller 1218. The logic power supply 1212 is also coupled to the controller 1218 and the current sensor 1216. The display 1214, the bypass button 1220, the plus button 1222 and the minus button 1224 are all also coupled to and controlled by the controller 1218.

In the embodiment shown, the remote test tool 1202 is coupled to the power source 1200, for example, a 24 volt power source of an irrigation controller. Other power sources or a built in power supply are utilized in alternative embodiments. However, the 24 volt power source from the irrigation controller is a convenient power source as it provides both power and access to the station wire. Because the moisture sensor unit 1206 is an integrated controller and sensor that is buried in soil, establishing communication with the moisture sensor unit 1206 through the station wire is advantageous. In prior systems, the control unit for the sensor is not integrated and is located above ground, thus the communication over the power line 1204 is not necessary. The remote test tool 1202 is coupled to the power line 1204 which is electrically coupled to the moisture sensor unit 1206. The moisture sensor unit 1206 is coupled to the common line 1208 and also is coupled to the solenoid 1211 through the actuation line 1209.

The remote test tool 1202 is generally used for a watering zone that is not currently operating (i.e., an irrigation controller is not currently supplying power over the station wire 1204 to the moisture sensor unit 1206).

In operation, the power supply 1200 provides power through the relay 1210 to the logic power supply 1212. The relay 1210, in accordance with the present embodiment, is a normally closed switch. The controller 1218 controls the relay 1210 by signaling the relay 1210 to open for short periods of time, for example 50 milliseconds at a time, causing one or more short power interruptions to be sent over the power line 1204. The logic power supply 1212 draws power from the current flowing to the moisture sensor unit 1206 and also stores power so that the controller 1218 continues operation during the power interruptions. The power interruptions are received at the moisture sensor 1206. The moisture sensor 1206 interprets the power interruptions such as described above with reference to FIG. 3. The bypass button 1220, the plus button 1222 and the minus button 1224 are used to send commands to the moisture sensor unit 1206. The display is used to show information received back from the moisture sensor unit 1206.

The current sensor 1216 detects pulses in the current flowing to the moisture sensor unit 1206. In order for the moisture sensor unit 1206 to communicate back to the remote test tool 1202, the moisture sensor unit 1206 will send pulses over the actuation line 1209 to the solenoid 1211. These pulses cause a change in the current that flows through the remote test tool 1202 to the moisture sensor unit 1206. The current sensor 1216 detects the change in current as increased current pulses. The microcontroller 1218 interprets the current pulses and displays the information on the display 1214. For example, the moisture sensor unit 1206, in one embodiment, communicates to the remote test tool a percentage water savings that is shown on the display 1214.

In accordance with one embodiment, the following communication sequences can be used to send commands to the moisture sensor unit from the remote test tool and receive information back from the moisture sensor unit. On power up of the remote test tool 1202 and the moisture sensor unit 1206 the remote test tool 1202 sends three pulses to put the moisture sensor unit 1206 into communication mode. Upon being put into communication mode, the moisture sensor unit 1206 returns status information (i.e., one pulse for disabled, two pulses for enabled, next two digit water savings, and finally a one digit offset setting). The remote test tool will display the water savings on the display. Upon pressing the plus button or the minus, the current offset is shown on the display. Upon pressing the plus button again, one pulse is sent to the moisture sensor to increase the offset by an incremental increase. Upon pressing the minus button, two pulses are sent to the moisture sensor unit to incrementally decrease the offset. Pressing the bypass button causes three pulses to be sent to the moisture sensor which toggles the state of the moisture sensor between enabled and disabled. Pressing the bypass button for at least 5 seconds causes four pulses to be sent which activates an advanced diagnostic mode. In the advance diagnostic mode pressing the plus key sends one pulse which causes the moisture sensor to send a piece of data. Pressing the minus key sends two pulses which causes the moisture sensor to send a previous piece of data. Pressing the bypass button and the minus button sends three pulses which cause a reset in a data log. Pressing the bypass button, the minus button and the plus button together send four pulses which reset the entire moisture sensor. Pressing the bypass button again for five seconds exits the advanced diagnostic mode. Other communication schemes may also be used in alternative embodiments.

Advantageously, the remote test tool 1202 can be utilized in conjunction with the moisture sensor unit 1206 in any existing irrigation system. However, in an alternative embodiment, the functionality of the remote test tool 1202 is implemented within an irrigation controller. For example, an irrigation controller (such as shown in FIGS. 1 and 2) can include the functional components of the remote test tool and communicate with a moisture sensor unit in the manner described above with reference to the remote test tool. Advantageously, in new irrigation systems that are being installed having the remote test tool functionality available within the irrigation controller remove the need for a separate testing and diagnostic device. Thus, the remote test tool and the irrigation controller are both examples of a remote or external device that may be used with or communicate with the moisture sensor unit 1206.

Figure 13:
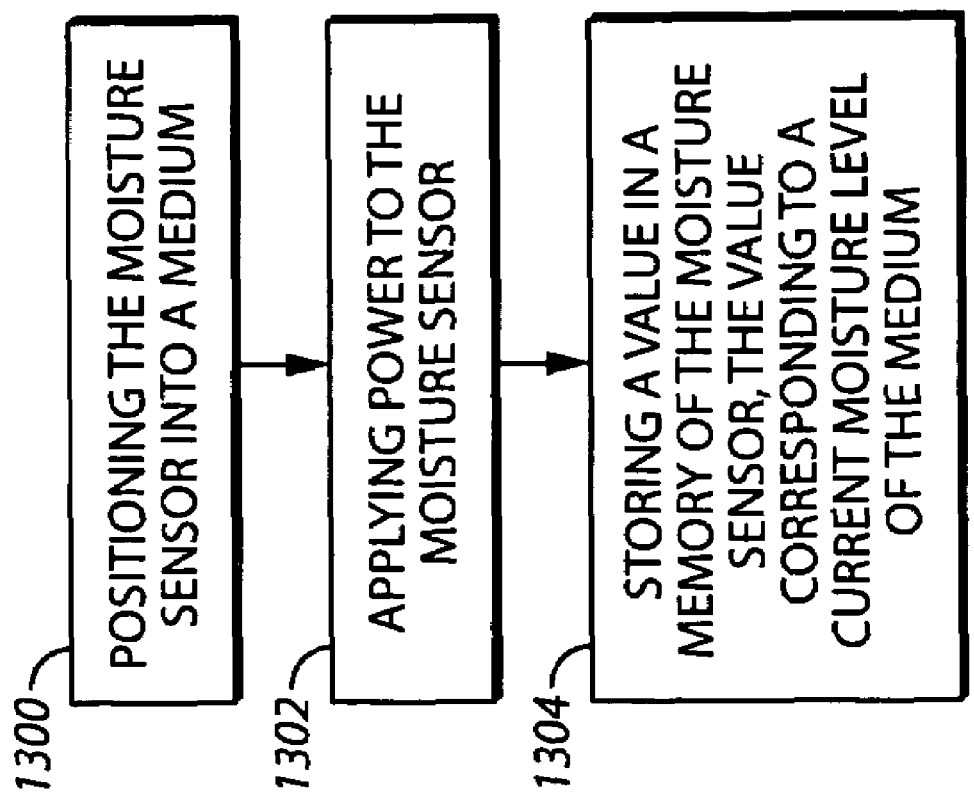
FIG. 13 is a flow diagram illustrating a method of calibrating a moisture sensor unit in accordance with one embodiment.

Referring to FIG. 13, a flow diagram is shown illustrating a method of calibrating a moisture sensor in accordance with one embodiment.

In step 1300, a moisture sensor is placed into a medium (for example, soil). Generally, the moisture sensor should be placed in an area that is representative of the soil for the entire watering zone, e.g., located near an irrigation valve to be controlled. The moisture sensor also is optionally placed horizontally in the irrigation zone at the bottom of a root zone (about 6 inches depth for turf). The soil surrounding the sensor is then carefully replaced to assure intimate contact between the soil and the moisture sensor. The soil is preferably compacted to the same degree as the surrounding undisturbed soil.

Next in step 1302, power is applied to the moisture sensor. In one embodiment, power is supplied for at least 1 minute to assure a proper reading. Following in step 1304, a value is measured and stored in a memory of the moisture sensor that corresponds to a current moisture level in the medium. In one embodiment, the medium is completely saturated with water such that the initial measured value is a saturated moisture level.

Optionally, an offset level is also stored in a memory of the moisture sensor. The offset level corresponds to a desired moisture level of the medium. In one embodiment, the offset level is stored as a value offset from the measured saturated moisture level. In various embodiments, the offset may be a positive or negative offset. Alternatively, the offset can be zero and the moisture sensor is calibrated to a threshold level equal to the initial measure moisture level. In a preferred form, the soil is saturated to a level considered the maximum level of saturation for the given soil type, and the stored threshold level is set to a desired negative offset from the saturated soil moisture level. Thus, irrigation is prevented at a desired point before the soil reaches completely saturated levels. Any offset and moisture level can be used in accordance with alternative embodiments in order to store a proper threshold level in the memory of the moisture sensor.

While the invention herein disclosed has been described by means of specific embodiments, examples, and applications thereof, other modifications, variations, and arrangements of the present invention may be made in accordance with the above teachings other than as specifically described to practice the invention within the spirit and scope defined by the following claims.

We claim:

1. An integrated moisture sensor and controller device adapted to be placed in soil comprising:
   a controller circuit for controlling a switch;
   a sensor circuit coupled to the controller circuit, the sensor circuit comprising a probe and adapted to provide the controller circuit a signal corresponding to a moisture level of the soil;
   wherein the controller circuit and the sensor circuit are integrated into a single device adapted to be positioned within the soil;
   the switch coupled to the controller circuit and adapted to be coupled to a power control line of an irrigation controller at an electrical position between the irrigation controller and a valve controlled by the irrigation controller, the power control line adapted to carry an activating power signal from the irrigation controller to the valve; and
   wherein the controller circuit comprises communication logic adapted to communicate with an external device.

2. The integrated moisture sensor and controller device of claim 1 wherein the communication logic includes means for detecting a power interrupt on the power control line.

3. The integrated moisture sensor and controller circuit of claim 1 wherein, upon control of the controller circuit, the switch is adapted to interrupt the power control line to interrupt irrigation.

4. The integrated moisture sensor and controller device of claim 1 further comprising a water tight housing enclosing the switch and the controller circuit.

5. The integrated moisture sensor and controller of claim 1 wherein the communication logic is adapted to receive commands from the external device.

6. The integrated moisture sensor and controller of claim 1 wherein the controller circuit is adapted to selectively cause interruption of irrigation based on the moisture level of the soil and a soil moisture threshold level; and
wherein the controller circuit is adapted to adjust the soil moisture threshold level based on a remote signal received by the communication logic.

7. The integrated moisture sensor and controller of claim 1 wherein the controller circuit is adapted to selectively cause interruption of irrigation based on the moisture level of the soil and a soil moisture threshold level; the integrated moisture sensor and controller further comprising:
a memory adapted to store data corresponding to one or more of the soil moisture threshold level and the moisture level of the soil.

8. The integrated moisture sensor and controller of claim 1 wherein the switch is adapted to interrupt irrigation in response to a signal from the controller circuit; and
wherein the controller circuit is adapted to determine an amount of time for which irrigation is interrupted.

9. The integrated moisture sensor and controller of claim 1 wherein the external device is an irrigation controller.

10. The integrated moisture sensor and controller of claim 1 wherein the external device is a remote test tool.

11. The integrated moisture sensor and controller device of claim 1 wherein the switch, the controller circuit and the sensor circuit are integrated into the single device.

12. The integrated moisture sensor and controller device of claim 11 further comprising:
a first connector coupled to the switch and adapted to couple the power control line from the irrigation controller to the switch; and
a second connector coupled to the switch and adapted to couple the power control line from the switch to the valve.

13. The integrated moisture sensor and controller of claim 1 wherein the switch is adapted to interrupt irrigation in response to a signal from the controller circuit; and
wherein the controller circuit is adapted to store a savings value corresponding to an amount of water savings.

14. The integrated moisture sensor and controller of claim 13 wherein the communication logic is adapted to send a signal corresponding to the savings value to the external device.

15. The integrated moisture sensor and controller of claim 14 wherein the saving value comprises a percentage water savings calculated by the controller circuit.

16. The integrated moisture sensor and controller device of claim 1 further comprising a housing enclosing the controller circuit.

17. The integrated moisture sensor and controller device of claim 16 wherein the housing comprises a waterproof housing enclosing the controller circuit.

18. The integrated moisture sensor and controller device of claim 16 wherein the controller circuit further comprises:
a variable frequency oscillator, a frequency of the variable frequency oscillator varies as a function of the capacitance of a capacitor within the sensor circuit, the capacitance varies as a function of the moisture content of the soil;
a reference oscillator; and
a logic circuit for comparing a frequency of the variable frequency oscillator to a frequency of the reference oscillator.

19. The integrated moisture sensor and controller device of claim 16 further comprising a logic power supply for providing power to the controller circuit and the switch.

20. The integrated moisture sensor and controller device of claim 16 further comprising:
a circuit board at least partially within the housing;
wherein the sensor circuit is formed on the circuit board, the sensor circuit including two electrodes forming a capacitor, a capacitance of the capacitor varies as a function of a moisture content of the soil;
wherein the controller circuit is attached to the circuit board;
wherein the housing comprises a waterproof housing adapted to prevent water from the soil from contacting the controller circuit.

21. The integrated moisture sensor and controller device of claim 16 further comprising a circuit board at least partially within the housing, wherein the controller circuit and the sensor circuit are attached to the circuit board.

22. The integrated moisture sensor and controller device of claim 16 further comprising a circuit board including a trace pattern formed on the circuit board, the trace pattern forming two electrodes of a capacitor, a capacitance of the capacitor varies as a function of a moisture content of soil.

23. The integrated moisture sensor and controller device of claim 22 wherein the circuit board is a multi-layer circuit board and wherein the trace pattern is formed on an inner layer of the multi-layer circuit board.

24. The integrated moisture sensor and controller device of claim 22 further comprising an insulating layer formed over the circuit board to seal the circuit board from the soil.

25. The integrated moisture sensor and controller device of claim 24 wherein the insulating layer comprises a coating formed around the circuit board.

26. The integrated moisture sensor and controller device of claim 24 wherein the insulating layer comprises a plastic sleeve formed around the circuit board.

27. An integrated moisture sensor and controller device adapted to be placed in soil comprising:
a controller circuit adapted to control operation of a switch;
a sensor circuit coupled to the controller circuit, the sensor circuit comprising a probe and adapted to provide the controller circuit a signal corresponding to a moisture level of the soil;
the switch coupled to the controller circuit;
a first connector coupled to the switch and adapted to couple a power control line from an external irrigation controller to the switch, the power control line for carrying an activating power signal from the external irrigation controller to a valve controlled by the external irrigation controller; and
a second connector coupled to the switch and adapted to couple the power control line from the switch to the valve;

wherein the controller circuit, the sensor circuit, the switch, the first connector, and the second connector are integrated into a single device adapted to be positioned within the soil;

wherein the switch is electrically positioned in a control signal path between the external irrigation controller and the valve;

wherein based upon the moisture level of the soil, the controller circuit controls operation of the switch to allow the activating power signal from the external irrigation controller to reach the valve or to interrupt the activating power signal from reaching valve; and wherein the controller circuit comprises communication logic adapted to communicate with an external device.

28. The integrated moisture sensor and controller device of claim 27 wherein the external device is an irrigation controller.

29. The integrated moisture sensor and controller device of claim 27 wherein the external device is a remote test tool.

30. The integrated moisture sensor and controller device of claim 27 wherein the communication logic is adapted to receive commands from the external device.

31. The integrated moisture sensor and controller device of claim 27 wherein the controller circuit is adapted to control operation of the switch based on the moisture level of the soil and a soil moisture threshold level; and wherein the controller circuit is adapted to adjust the soil moisture threshold level based on a remote signal received by the communication logic.

32. The integrated moisture sensor and controller device of claim 27 wherein the controller circuit is adapted to control operation of the switch based on the moisture level of the soil and a soil moisture threshold level; the integrated moisture sensor and controller further comprising:

a memory adapted to store data corresponding to one or more of the soil moisture threshold level and the moisture level of the soil.

33. The integrated moisture sensor and controller device of claim 27 wherein the switch is adapted to interrupt irrigation in response to a signal from the controller circuit; and wherein the controller circuit is adapted to determine an amount of time for which irrigation is interrupted.

34. The integrated moisture sensor and controller device of claim 27 wherein the controller circuit is adapted to store a savings value corresponding to an amount of water savings due to the interruption of the activating power signal.

35. The integrated moisture sensor and controller device of claim 34 wherein the communication logic is adapted to send a signal corresponding to the savings value to the external device.

36. The integrated moisture sensor and controller device of claim 35 wherein the saving value comprises a percentage water savings calculated by the controller circuit.

37. An integrated moisture sensor and controller device adapted to be placed in soil comprising:

a controller circuit for controlling actuation of a valve;

a sensor circuit coupled to the controller circuit, the sensor circuit comprising a probe and adapted to provide the controller circuit a signal corresponding to a moisture level of the soil;

wherein the controller circuit and the sensor circuit are integrated into a single device adapted to be positioned within the soil;

a switch coupled to the controller circuit and adapted to be coupled to a power control line of an irrigation controller that controls the valve, the power control line adapted to carry an activating power signal from the irrigation controller to the valve; and wherein the controller circuit comprises communication logic adapted to receive commands from an external device.

38. An integrated moisture sensor and controller device adapted to be placed in soil comprising:

a controller circuit for controlling actuation of a valve;

a sensor circuit coupled to the controller circuit, the sensor circuit comprising a probe and adapted to provide the controller circuit a signal corresponding to a moisture level of the soil;

wherein the controller circuit and the sensor circuit are integrated into a single device adapted to be positioned within the soil;

a switch coupled to the controller circuit and adapted to be coupled to a power control line of an irrigation controller that controls the valve, the power control line adapted to carry an activating power signal from the irrigation controller to the valve;

wherein the controller circuit is adapted to selectively cause interruption of irrigation based on the moisture level of the soil and a soil moisture threshold level; and wherein the controller circuit is adapted to adjust the soil moisture threshold level based on a remotely received signal.

39. An integrated moisture sensor and controller device adapted to be placed in soil comprising:

a controller circuit adapted to control operation of a switch;

a sensor circuit coupled to the controller circuit, the sensor circuit comprising a probe and adapted to provide the controller circuit a signal corresponding to a moisture level of the soil;

the switch coupled to the controller circuit;

a first connector coupled to the switch and adapted to couple a power control line from an external irrigation controller to the switch, the power control line for carrying an activating power signal from the external irrigation controller to a valve controlled by the external irrigation controller; and a second connector coupled to the switch and adapted to couple the power control line from the switch to the valve;

wherein the controller circuit, the sensor circuit, the switch, the first connector, and the second connector are integrated into a single device adapted to be positioned within the soil;

wherein the switch is electrically positioned in a control signal path between the external irrigation controller and the valve;

wherein based upon the moisture level of the soil, the controller circuit controls operation of the switch to allow the activating power signal from the external irrigation controller to reach the valve or to interrupt the activating power signal from reaching the valve; and wherein the controller circuit comprises communication logic adapted to receive commands from an external device.

40. An integrated moisture sensor and controller device adapted to be placed in soil comprising:

a controller circuit adapted to control operation of a switch;

a sensor circuit coupled to the controller circuit, the sensor circuit comprising a probe and adapted to provide the controller circuit a signal corresponding to a moisture level of the soil;

the switch coupled to the controller circuit;

a first connector coupled to the switch and adapted to couple a power control line from an external irrigation controller to the switch, the power control line for carrying an activating power signal from the external irrigation controller to a valve controlled by the external irrigation controller; and a second connector coupled to the switch and adapted to couple the power control line from the switch to the valve;

wherein the controller circuit, the sensor circuit, the switch, the first connector, and the second connector are integrated into a single device adapted to be positioned within the soil;

wherein the switch is electrically positioned in a control signal path between the external irrigation controller and the valve;

wherein based upon the moisture level of the soil and a soil moisture threshold level, the controller circuit controls operation of the switch to allow the activating power signal from the external irrigation controller to reach the valve or to interrupt the activating power signal from reaching the valve;

wherein the controller circuit is adapted to adjust the soil moisture threshold level based on a remote signal received by communication logic.

* * * * *